United States Patent [19]

Schumann

[11] Patent Number: Plant 7,391

[45] Date of Patent: Dec. 11, 1990

[54] GERANIUM PLANT NAMED FISMANON

[75] Inventor: Ingeborg Schumann, Hoehr-Grenzhausen, Fed. Rep. of Germany

[73] Assignee: Florfis AG, Binningen, Switzerland

[21] Appl. No.: 426,193

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Geranium plant named Fismanon, particularly characterized by the combined features of rose colored semi-double flowers, very early flowering, rich in flowers in summer, unique leaf shape, compact habit, and fast rooting.

1 Drawing Sheet

The present invention comprises a new and distinct cultivar of Geranium, botanically known as *Pelargonium peltatum,* and commercially known as ivy Geranium. The new cultivar is known by the cultivar name Fismanon.

Fismanon is a product of a planned breeding program which had the objective of creating new ivy Geranium cultivars with rose flower color, very fast rooting, compact habit for hanging baskets, and a unique type of leaf.

Fismanon was originated from a hybridization made by the inventor in a controlled breeding program in Galdar, Gran Canaria, Spain in 1982. The female parent was Mad. Crousse, a cultivar having light red semi-double flowers and long internotes. The male parent of Fismanon was an inbred line of the cultivar Super Rose, having salmon rose semi-double flowers and short internodes.

Fismanon was discovered and selected as one flowering plant within the progeny of the stated cross by Ingeborg Schumann in January 1983 in a controlled environment in Galdar, Gran Canaria, Spain.

The first act of asexual reproduction of Fismanon was accomplished when vegetative cuttings were taken from the initial selection in February 1985 in a controlled environment in Gran Canaria by, or under the supervision of, Ingeborg Schumann.

Horticultural examination of selected units initiated in the spring of 1985 and continuing thereafter has demonstrated that the combination of characteristics as herein disclosed for Fismanon are firmly fixed and are retained through successive generations of asexual reproduction.

Fismanon has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse conditions which approximate those generally used in commercial practice.

The following traits have been repeatedly observed and are determined to be basic characteristics of Fismanon, which, in combination, distinguish this Geranium as a new and distinct cultivar:

1. Rose colored semi-double flowers.

2. New shape of leaf; as compared with other *peltatum* varieties, there is a stronger degree of lobing, deeper incisions, and pointed tips.
3. Compact habit for hanging baskets.
4. Very good rooting.
5. Very early flowering.

Of the many commercial cultivars known to the present inventor, the most similar in comparison to Fismanon is Pink Charme. Reference is made to attached Chart A which compares certain characteristics of Fismanon to those same characteristics of Pink Charme. In general comparison to Pink Charme, Fismanon has a darker flower color and shorter internodes, earlier commencement of flowering, more flowers during the summer, and different leaf shape.

The accompanying photographic drawing shows typical flower and foliage characteristics of Fismanon, with the colors being as true as possible with illustrations of this type. The sheet is a color photograph showing the flowers, buds, and foliage of a typical plant of Fismanon.

In the following description color references are made to The Royal Horticultural Society Color Chart (RHS) and in certain instances to the Horticultural Color Chart (HCC). The color values were determined between 8:00 a.m. and 9:00 a.m. indoors on May 20, 1987 under 40,000 Lux light intensity at Hillscheid, Federal Republic of German.

Classification:

*Botanical.*—*Pelargonium peltatum* l'hert. cv Fismanon.

*Commercial.*—Ivy geranium.

INFLORESCENCE

A. Umbel:

*Average diameter.*—Indoor, 8.3 cm; outdoor, 8.5 cm.

*Average depth.*—Indoor, 4.9 cm; outdoor, 5.1 cm.

*Peduncle length.*—Indoor, 12.2 cm; outdoor, 10.4 cm.

*Pedical length.*—Indoor, 2.7 cm; outdoor, 2.3 cm.

*Pedicels.*—Formed partly with "spurs" (swellings).

B. Corolla:

*Average diameter.*—Indoor, 5.4 cm; outdoor, 5.1 cm.

*Form.*—Semi-double.

*Color (general tonality from a distance of three meters).*—Pink, 62B-C.

*Color (upper surface, main color).*—RHS 67D; HCC 625/1.

*Color (upper surface, near margin).*—RHS 62B; HCC 625/2; lower surface not noticeably different; the upper petal has purple stripes and a white spot at the base.

C. Bud:

*Shape.*—narrow, elliptic.

*Color.*—light green.

D. Reproductive organs:

*Androecium.*—8 anthers.

*Gynoecium.*—5 lobed stigma.

E. Spring flowering response period: In Hillscheid, Federal Republic of Germany in 1988, 75% of plants with at least 1 flower opened 10 weeks after planting of unrooted cuttings in week 7.

F. Outdoor flower production: The flower count in 1988 in Hillscheid, Federal Republic of Germany indicated between 53 and 58 flowers per plant for June through October observation period.

G. Durability: Rain resistance is not very good; shattering medium.

PLANT

A. Foliage:

*Form.*—Ivy shaped.

*Margin.*—Entire; but certain leaf segments notched at periphery.

*Color.*—Medium green, approximately RHS 147B.

*Zonation.*—None.

*Tolerance to botrytis.*—Medium.

B. General appearance and form:

*Internode length.*—Very short.

*Branching pattern.*—5.9 branches per plant 13 weeks after planting of unrooted cuttings.

*Height.*—Compact, small.

CHART A

COMPARISON OF FISMANON AND PINK CHARME

| | FISMANON | PINK CHARM |
|---|---|---|
| Color of leaves | light-medium green | medium green |
| Zonation | absent | medium |
| Color of flower petals | rose, RHS 62B-67D | light rose, RHS 62B-C |
| Markings on petal | medium | medium-strong |
| Markings on lower side of petal | stripes hardly visible | marked stripes |
| Pedicel swelling | present | absent |
| Sepals and pedicels | green | green, partly red |
| Internode length | 3.0 cm | 6.1 cm |
| Beginning of flowering | early | medium-late |

I claim:

1. A new and distinct cultivar of Geranium plant named Fismanon, as illustrated and described.

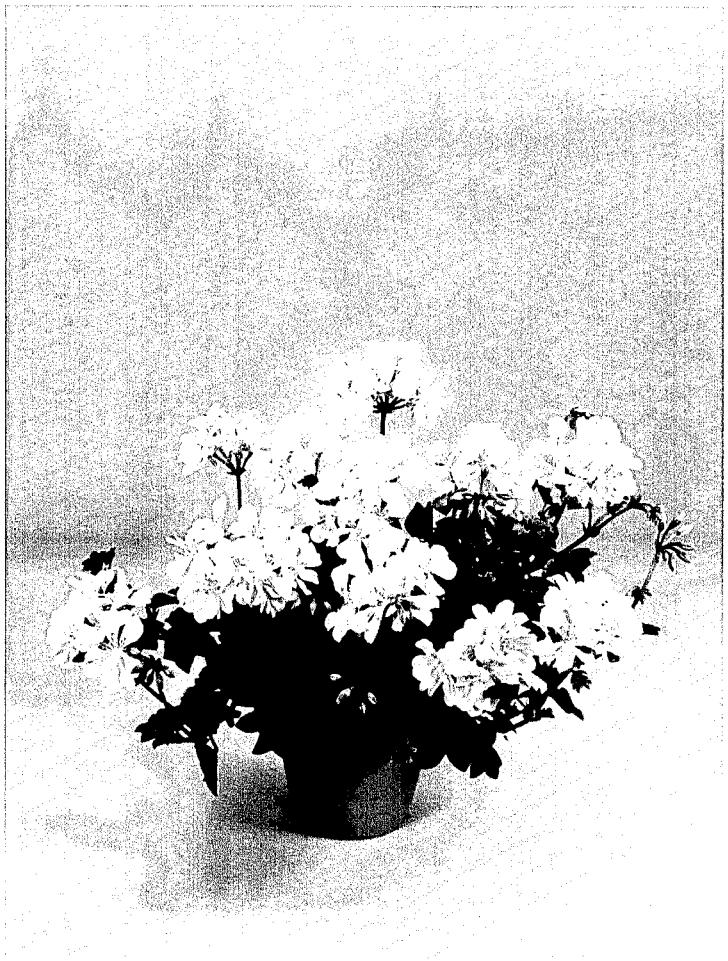

* * * * *